United States Patent
Does et al.

(10) Patent No.: US 8,923,948 B2
(45) Date of Patent: Dec. 30, 2014

(54) SYSTEM AND METHOD FOR DETERMINING MECHANICAL PROPERTIES OF BONE STRUCTURES

(75) Inventors: Mark Does, Nashville, TN (US); Robert Adam Horch, Nashville, TN (US); Jeffrey S. Nyman, Nashville, TN (US); Daniel Frank Gochberg, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 783 days.

(21) Appl. No.: 13/151,556

(22) Filed: Jun. 2, 2011

(65) Prior Publication Data
US 2012/0029340 A1 Feb. 2, 2012

Related U.S. Application Data

(60) Provisional application No. 61/369,248, filed on Jul. 30, 2010, provisional application No. 61/482,922, filed on May 5, 2011.

(51) Int. Cl.
*A61B 5/055* (2006.01)
*G01R 33/44* (2006.01)
*G01R 33/48* (2006.01)

(52) U.S. Cl.
CPC .......... *G01R 33/448* (2013.01); *G01R 33/4816* (2013.01)
USPC ............................ 600/410; 324/307; 324/309

(58) Field of Classification Search
USPC .......... 600/410–411; 324/307, 309–310, 312; 436/173
See application file for complete search history.

(56) References Cited

U.S. PATENT DOCUMENTS

| | | | |
|---|---|---|---|
| 6,943,549 B2 * | 9/2005 | Matsuo et al. | 324/309 |
| 7,574,248 B2 * | 8/2009 | Ackerman et al. | 600/410 |
| 8,000,766 B2 * | 8/2011 | Lang et al. | 600/407 |
| 2003/0057947 A1 * | 3/2003 | Ni et al. | 324/309 |
| 2006/0100498 A1 * | 5/2006 | Boyce et al. | 600/408 |
| 2011/0208033 A1 * | 8/2011 | Nicolella et al. | 600/407 |
| 2012/0076378 A1 * | 3/2012 | Keereman et al. | 382/131 |

OTHER PUBLICATIONS

Benjamin and Ralphs, "Fibrocartilage in tendons and ligaments—an adaptation to compressive load," J Anat (1998) 193: 481-494.
Bergin et al., "Lung parenchyma: Projection reconstruction MR imaging," Radiology (1991) 179: 771-781.
Bergin et al., "MR imaging of lung parenchyma: A solution to susceptibility," Radiology (1992) 183: 673-676.

(Continued)

*Primary Examiner* — Ruth S Smith
(74) *Attorney, Agent, or Firm* — Novak Druce Connolly Bove + Quigg LLP; Eduardo J. Quinones

(57) ABSTRACT

Systems and methods for characterizing bone structures are provided for characterizing bone structures. In the system and method, one or more $^1$H NMR or MRI signals associated with a bone structure are obtained. Thereafter one or more signal parameters are computed from the obtained signals, where each of the signal parameters comprising at least one of a relaxation rate constant or a corresponding signal amplitude associated with a component of the obtained signals defined by a $T_2$ value or a range of $T_2$ values. Finally, the mechanical properties or fracture risk for the bone structure are determined based on the computed signal parameters and stored correlation data.

16 Claims, 11 Drawing Sheets

(56) References Cited

OTHER PUBLICATIONS

Brossman et al., "Short echo time projection reconstruction MR imaging of cartilage with histopathologic correlation: comparison with fat-suppressed spoiled GRASS and magnetization transfer contrast MR imaging," Radiology (1997) 203: 501-507.
Burghardt et al., "Age- and gender-related differences in the geometric properties and biomechanical significance of intracortical porosity in the distal radius and Tibia," J Bone Miner Res (May 2010) 25: 983-993.
Carter et al., "New approaches for interpreting projected bone densitometry data," J Bone Miner Res (Feb. 1992) 7:137-145.
Chappell et al., "Clinical imaging of the liver with ultrashort TE pulse sequences," Proc Int Soc Mgn Reson Med (2003): 1418.
Du et al., "Dual inversion recovery, ultrashort echo time (DIR UTE) imaging: Creating high contract for short-T-2 species," Magnetic Resonance in Medicine (Feb. 2010) 63: 447-455.
Du et al., "Qualitative and quantitative ultrashort echo time (UTE) imaging of cortical bone," J Magn. Reson. (2010) 207(2): 304-311.
Edelstein et al., "NMR imaging at 5.1 MHz: Work in progress," In NMR Imaging: Winston Salem, NC Bowman Gray School of Medicine (1982): 139-146.
Fenricht et al., "Relaxation times and microstructures," NMR Biomed (2001) 14: 133-139.
Fernandez-Seara et al., "Water content measured by proton-deuteron exchange NMR predicts bone mineral density and mechanical properties," J Bone Miner Res (Feb. 2004) 19: 289-296.
Frank et al., "Mapping the physiological parameters of articular cartilage with magnetic resonance imaging," Top Magn Reson Imaging (1999) 10: 153-179.
Gatehouse and Bydder, "Magnetic resonance imaging of short $T_2$ components in tissues," Clin Radiol (2003) 58: 1-19.
Gatehouse et al., "Clinical imaging of the brain with ultrashort TE (UTE) pulse sequences," Proc Int Soc Magn Reson Med (2003): 2268.
Gatehouse et al., "Imaging of the knee with ultrashort TE (UTE) pulse sequences," Proc Int Soc Magn Reson Med (2003) 11: 111.
Gold et al., "Characterization of atherosclerotic plaque at 1.5T," J Magn Reson Imaging (1993) 3: 399-407.
Gold et al., "In vivo short echo time imaging of Achilles Tendon," Proc Int Soc of Magn Reson Med (2001) 9: 244.
Gold et al., "MR imaging of the articular cartilage of the knee: New methods using ultrashort TE's," Am J Roentgenol (1998) 170: 1223-1226.
Gold et al., "MR spectroscopic imaging of collagen: Tendons and knee menisci," Magn Reson Med (1995) 34: 647-654.
Gold et al., "Short echo time MR spectroscopic imaging of the lung parenchyma," J Magn Reson Imaging (2002) 15: 679-684.
Grandinetti, "Nuclear magnetic resonance for the people," 2009. (74 pages).
Harrison et al., "Magnetization transfer and $T_2$ relaxation components in tissue," Magn Reson Med (1995) 33: 490-496.
Hauger et al., "Characterization of the 'red zone' on knee meniscus: MR imaging and histologic correlation," Radiology (2000) 217: 193-200.
Hayes and Parellada, "The magic angle effect in musculoskeletal MR imaging," Top Magn Reson Imaging (1996) 8: 51-56.
Henkelman et al., "Anisotropy of NMR properties of tissue," Magn Reson Med (1994) 32: 592-602.
Henkelman et al., "Magnetization transfer in MRI: A review," NMR Biomed. (2001) 14: 57-64.
Johnell et al., "Predictive value of BMD for hip and other fractures," Journal of Bone and Mineral Research (Jul. 2005) 20: 1185-1194.
Kanis et al., "Ten year probabilities of osteoporotic fractures according to BMD and diagnostic thresholds," Osteoporos Int (Dec. 2001) 12: 989-995.
Larson et al., "Using adiabatic inversion pulses for long-T-2 suppression in ultrashort echo time (UTE) imaging," Mag Res Med (Nov. 2007) 58: 952-961.
Lu et al., "Improved spectral selectivity and reduced susceptibility in true-FISP using a near zero TE undersampled 3D PR sequence," Proc Int Soc Magn Reson Med (2002): 470.
Majumdar et al., "High-resolution magnetic resonance imaging: Three-dimensional trabecular bone architecture and biomechanical properties," Bone (May 1998) 22:445-454.
Majumdar, "Magnetic resonance imaging for osteoporosis," Skeletal Radiol (Feb. 2008) 37: 95-97.
Nayak et al., "Imaging ultrashort $T_2$ species in the brain," Proc Int Soc Magn Reson Med (2000): 509.
Neilson et al., "Ultrashort echo time 2D time of flight MR angiography using a half-pulse excitation," Magn Reson Med (1999) 41: 591-599.
Nyman et al., "Effect of ultrastructural changes on the toughness of bone," Micron (2005) 36: 566-582.
Nyman et al., "Measurements of mobile and bound water by nuclear magnetic resonance correlate with mechanical properties of bone," Bone (Jan. 2008) 42:193-199.
Nyman et al., "The influence of water removal on the strength and toughness of cortical bone," Journal of Biomechanics (2006) 39: 931-938.
Oatridge et al., "Magic angle imaging of the Achilles tendon in patients with chronic tendonopathy," Clin Radiol (2003) 58: 384-388.
Oatridge et al., "Magnetic resonance: Magic angle imaging of the Achilles tendon," Lancet. (2001) 358: 1610-1611.
Ouwerkerk et al., "Tissue sodium concentration in human brain tumors as measured with $^{23}$Na MR imaging," Radiology (2003) 227: 529-537.
Pauly et al., "Suppression of long $T_2$ components for short $T_2$ imaging," J Magn Reson Imaging (1992) 2: 145.
Pruessmann et al., "Advances in sensitivity encoding with arbitrary k-space trajectories," Magn Reson Med (2001) 46: 638-651.
Rahmer et al., "Selective 3D ultrashort TE imaging: Comparison of 'dual-echo' acquisition and magnetization preparation for improving short-T-2 contrast," Magnetic Resonance Materials in Physics Biology and Medicine (Apr. 2007) 20: 83-92.
Reichert et al., "Proton imaging of periosteum and cortical bone with ultrashort TE pulse sequences," Proc Int Soc Magn Reson Med (2003) 11: 451.
Robson and Bydder, "Clinical ultrashort echo time imaging of bone and other connective tissues," NMR in Biomedicine (2006) 19: 765-780.
Robson et al., "Human in vivo imaging of phosphorus in cortical bone using ultrashort TE pulse sequences," Proc Int Soc Magn Reson Med (2003) 11: 791.
Schmidt et al., "FID-based lung MRI at 0.5T: Theoretical considerations and practical implications," Magn Reson Med (1998) 39: 666-672.
Sigmund et al., "Diffusion-based MR methods for bone structure and evolution," Magn. Reson. Med (Jan. 2008) 59: 28-39.
Silver et al., "Highly selective Pi/2 and Pi-pulse generation," Journal of Magnetic Resonance (1984) 59: 347-351.
Smith, "Clinical application of NMR tomographic imaging," In NMR Imaging: Winston Salem, NC Bowman Gray School of Medicine (1982): 125-132.
Techawiboonwong et al., "Cortical bone water: In vivo quantification with ultrashort echo-time MR imaging," Radiology (2008) 248(3): 824-833.
Thulborn et al., "Quantitative tissue sodium concentration mapping of the growth focal cerebral tumors with sodium magnetic resonance imaging," Magn Reson Med (1999) 41: 351-359.
Vestergaard, "Discrepancies in bone mineral density and fracture risk in patients with type 1 and type 2 diabetes—A meta-analysis," Osteoporos in (Apr. 2007) 18: 427-444.
Wehrli, "Structural and functional assessment of trabecular and cortical bone by micro magnetic resonance imaging," J Magn Reson Imaging (Feb. 2007) 25: 390-409.
Whittall and Mackay, "Quantitative interpretation of NMR relaxation data," Journal of Magnetic Resonance (1989) 84: 134-152.

* cited by examiner

SYSTEM AND METHOD FOR DETERMINING MECHANICAL PROPERTIES OF BONE STRUCTURES

CROSS REFERENCE TO RELATED APPLICATIONS

This application claims the benefit of Provisional Application Ser. No. 61/369,248 entitled "SYSTEM AND METHOD FOR DETERMINING MECHANICAL PROPERTIES AND FRACTURE RISK COF BONE STRUCTURES BASED ON 1H NMR OR MRI CHARACTERISTICS", filed Jul. 30, 2010, and Provisional Application Ser. No. 61/482,922 entitled "SYSTEM AND METHOD FOR CHARACTERIZING BIOLOGICAL TISSUES USING MAGNETIC RESONANCE-DERIVED PROTON CONCENTRATIONS", filed May 5, 2011, the contents of which are herein both incorporated by reference in their entirety.

STATEMENT REGARDING FEDERALLY SPONSORED RESEARCH

This invention was made with government support under grant numbers EB001744 and EB001452 awarded by the National Institutes of Health and grant number NSF 0448915 awarded by the National Science Foundation. The government has certain rights in the invention.

FIELD OF THE INVENTION

The present invention relates to bone diagnostics, and more specifically to system and methods for determining the mechanical properties of bone structures.

BACKGROUND

In general, current bone diagnostic techniques for assessing the mechanical properties of bone structure and, more importantly, fracture risk are inadequate. The estimate of areal bone mineral density (BMD) by dual energy x-ray absorptiometry (DXA) does not reliably predict fracture risk. In fact, for a given DXA score, there is an unexplained increase in fracture risk with age, as well as with progression of various disease states, such as diabetes. These limitations of DXA related to BMD depending on bone size may be somewhat overcome by quantitative computed tomography imaging. However, any X-ray based diagnostic technique is generally sensitive primarily to the mineral portion of a bone structure, which accounts for only ≈43% of the bone structure by volume. The remaining soft-tissue components of bone structures, including collagen and collagen-bound water, are essentially invisible to DXA and quantitative computed tomography. Accordingly, there exists a need for supplementing or replacing DXA and other techniques in order to more accurately predict fracture risks.

SUMMARY

Embodiments of the invention concern systems and methods for characterizing bone structures. In a first embodiment, a method for characterizing bone structures is provided. The method includes obtaining one or more $^1$H NMR or MRI signals associated with a bone structure and computing one or more signal parameters from the obtained signals, where each of the signal parameters comprising at least one of a relaxation rate constant or a corresponding signal amplitude associated with a component of the obtained signals defined by a $T_2$ value or a range of $T_2$ values. The method also includes determining mechanical properties or fracture risk for the bone structure based on the computed signal parameters and stored correlation data.

In a second embodiment of the invention, a system for characterizing bone structures is provided. The system includes an imaging device for generating one or more $^1$H NMR or MRI signals associated with a bone structure. The system further includes a processing element communicatively coupled to the imaging device. In the system, the processing element is configured for computing one or more signal parameters from the obtained signals, where each of the signal parameters comprising at least one of a relaxation rate constant or corresponding signal amplitude associated with a component of the obtained signals defined by a $T_2$ value or a range of $T_2$ values. The processing element is also configured for determining the mechanical properties or fracture risk for the bone structure based on the computed signal parameters and stored correlation data.

In a third embodiment of the invention, a method of characterizing bone structures is provided. The method includes obtaining magnetic resonance (MR) data for a region of interest (ROI) and a reference, the MR data based on a time-varying magnetic field configured to cause the MR data to be dominated by a first type of water protons in the ROI, wherein at least an apparent proton concentration and a $T_1$ time of the reference are known. The method also includes extracting a proton density value for the reference based at least on the MR data, parameters associated with the pulse sequence, and the known T1 time. The method further includes extracting a proton density value for the ROI based at least on the MR data, the parameters associated with the pulse sequence, and an average T1 value for a type of biological tissue associated with the ROI. The method additionally includes determining an apparent proton concentration for the ROI based on the apparent proton concentration for the reference, the proton density for the reference, and the proton density for the ROI.

In a fourth embodiment of the invention, a system for characterizing bone structures is provided. The system includes a storage element for receiving magnetic resonance (MR) data for a biological tissue of interest and a calibration sample, the MR data based on a time-varying magnetic field configured to cause the MR data to be dominated by a first type of water protons in the biological tissue, and the calibration sample having at least a known water proton concentration and a known $T_1$ time. The system also includes a processing element communicatively coupled to the storage element. In the system, the processing element is configured for extracting a proton density value for the reference based at least on the MR data, parameters associated with the pulse sequence and the known T1 time. The processing element is also configured for extracting a proton density value for the ROI based at least on the MR data, the parameters associated with pulse sequence, and an average T1 value for a type of biological tissue associated with the ROT. The system is further configured for determining an apparent proton concentration for the ROI based on the apparent proton concentration for the reference, the proton density for the reference, and the proton density for the ROI.

DETAILED DESCRIPTION

Figure 1A:
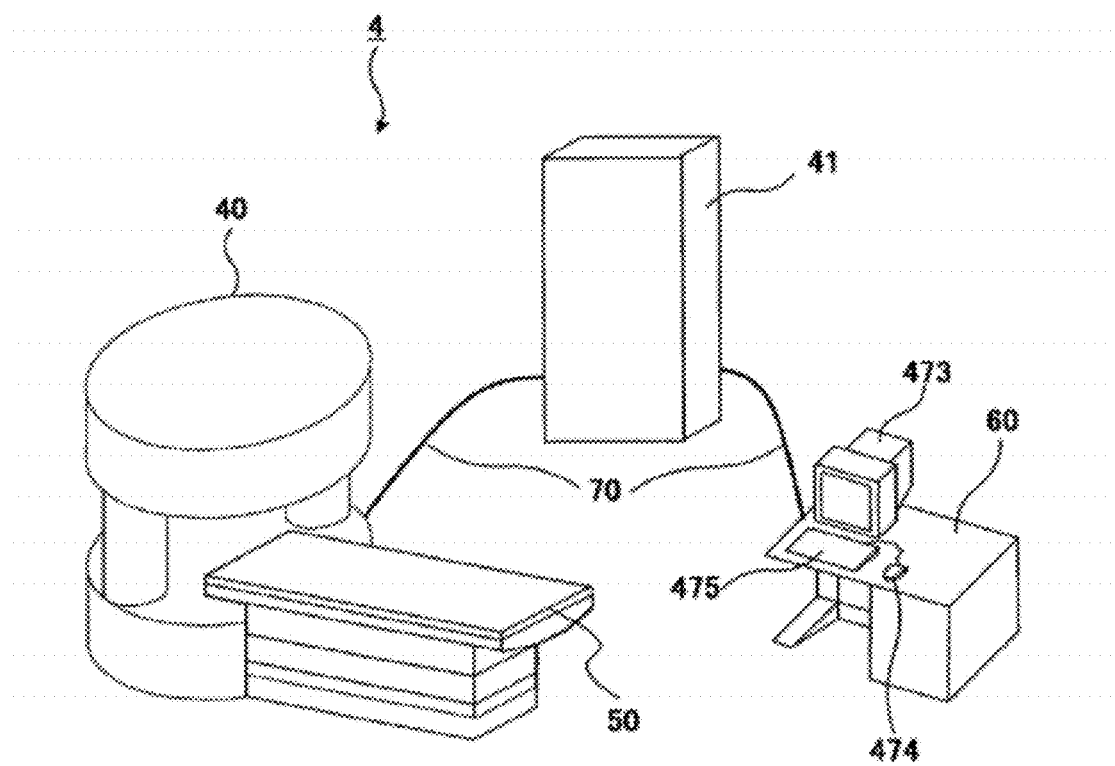
FIG. 1A is a structural diagram showing an MRI apparatus in accordance with the various embodiments.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

As described above, conventional bone diagnostic techniques are generally limited with respect to being able to accurately predict fracture risks. In particular, most conventional techniques tend to be inaccurate since they rely primarily, if not exclusively, on bone mineral content. That is, these conventional techniques generally ignore the impact of other properties and types of tissues in bone structures. For example, these techniques generally ignore the presence of collagen in bone structures and the hydration-state of this collagen in the bone structures, which can significantly affect mechanical properties and thus fracture risk.

As a surrogate to ionizing-radiation-based computed tomography (CT), magnetic resonance imaging (MRI) techniques have been developed to characterize trabecular volume and architecture as a means to assess fracture risk. In these techniques, MRI-derived measurements of bone volume fraction and trabecular thickness correlated with the compressive strength of human trabecular bone. However, the correlations were not as strong as that between CT-derived BMD and strength. Further, these MRI techniques do not assess the inherent quality of the bone tissue, a significant shortcoming given the importance of ultrastructural characteristics of the extracellular matrix (e.g., collagen integrity) to the fracture resistance of bone.

One proposed solution for characterizing bone structures using MRI techniques has been to obtain nuclear magnetic resonance (NMR) measurements during MRI imaging and attempt to correlate such measurements to mechanical properties of bone. However, these methods have met with only limited success. For example, using ex vivo studies of bone, various quantifications of water by NMR have been correlated with the mechanical competence of bone. In a rabbit model of diet-induced hypomineralization, a $^1$H NMR-derived measurement of water content was directly related to the bending strength of cortical bone. However, in a study of ovariectomized and treated mice, only group-mean total water $^1$H NMR signal correlated with mechanical properties. That is, no correlation was found across pooled data from different bones. In another NMR technique known as "decay from diffusion in an internal field" (DDIF), an inverse correlation was found between this NMR-derived pore water parameter and the yield stress of bovine trabecular bone in compression, but provided only rough agreement to pore-water.

In yet another study, an attempt was made to correlate NMR measurements of both pore water and water bound to the extracellular matrix to the mechanical properties of human bone using $T_2^*$-discriminated $^1$H NMR signals at low static magnetic field. In this study, while a direct relationship existed between the so-called $T_2^*$-defined bound water and peak stress, the measurement described a low fraction of the peak stress variance ($r^2$=0.36). Also, the translation of $T_2^*$ based discrimination to clinical imaging may be problematic due to the presence of lipid in bone, and the inability of $T_2^*$ to discriminate bone HT pools at clinical field strengths. For instance, studies have found that no discrimination was found at clinical fields strengths (≥1.5 T).

The main limitation of the previous attempted characterization methods has been the failure to use $^1$H NMR signals that can discriminate properly between different types of water protons in bone structures. As a result, without such discrimination, it is not possible to consider solely the microanatomical compartments that most strongly affect mechanical properties. In view of these limitations, the various embodiments provide methods for characterizing the mechanical properties of bone structures based on measurements of $T_2$ $^1$H NMR signals. In particular, clinical magnetic resonance imaging (MRI) techniques are used in the various embodiments to obtain $^1$H NMR signals that can be correlated to mechanical properties and fracture risk. Specifically, clinical MRI signals are characterized by $^1$H NMR transverse relaxation time constants ($T_2$) that distinguish or discriminate between proton signals from collagen, collagen-bound water, and pore water. The discriminated $T_2$ signals can then be used to obtain water proton concentrations fix collagen bound water protons and water protons in pores or lipid protons. These concentrations, together with correlation data, can then be used in the various embodiments to obtain estimates of the mechanical properties of bone structures. Accordingly, this provides a non-invasive assessment of the mechanical properties of bones with significant accuracy over conventional techniques as it is not limited solely to bone mineral density measurements.

Figure 1B:
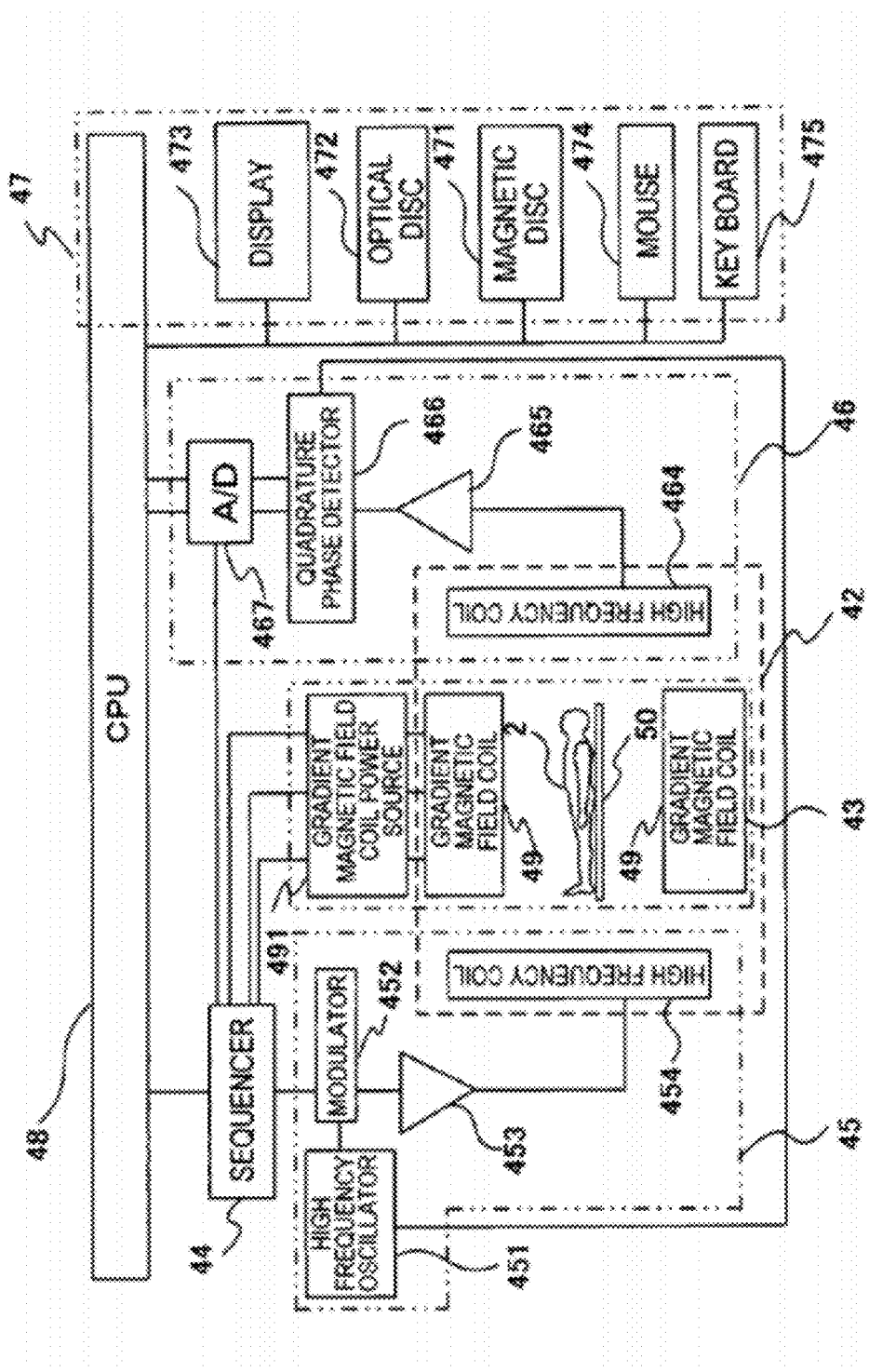
FIG. 1B is a block diagram to show the interior of the MRI apparatus in FIG. 1A.
Figure 13:
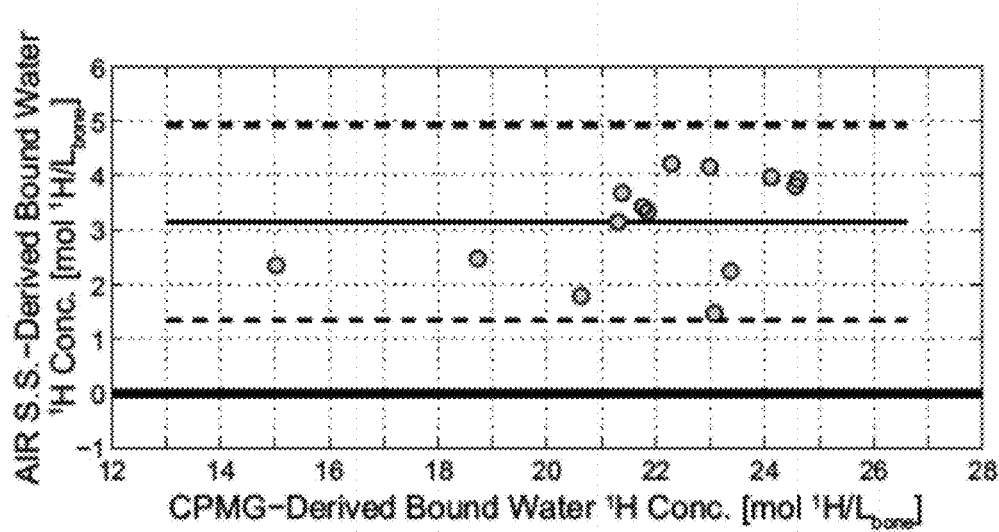
FIG. 13 is an x-y plot of CPMG-derived bound water proton concentration versus AIR SS derived bound water proton concentration.

Turning first to FIGS. 1A and 1B, an MRI apparatus configured for carrying out the various embodiments of the invention will be described. FIG. 1A is a structural diagram showing an MRI apparatus in accordance with the various embodiments, and FIG. 13 is a block diagram to show the interior of the MRI apparatus in FIG. 1A.

The MRI apparatus 4 of FIG. 1A is of a perpendicular magnetic field type (open type), but may be of any other type such as a tunnel type. In the MRI apparatus 4, a oscillating magnetic field (electromagnetic waves) is applied to a subject arranged in static magnetic fields to induce nuclear magnetic resonance (NM R). A detecting coil (RF coil) detects resonance signals as electrical signals, thereby the signals are reconstructed as projected data to produce an image of the interior of the subject 2 noninvasively.

The MRI apparatus 4 comprises a gantry 40, a house 41 in which a power source to drive various devices in the gantry 40 and various control devices to control are stored, a bed 50 on which the above subject 2 is rested, and a processing unit 60 which processes the received NMR signals to reconstruct a tomogram image of the subject 2. The gantry 40 and the house 41 are connected by a power source/signal line 70. Similarly, the processing unit 60 and the house 41 are connected by a power source/signal line 70.

The gantry 40 and the bed 50 are placed in a shield room to shield high frequency electromagnetic waves and static magnetic fields (not shown). The house 41 and the processing unit 60 are placed outside of the shield room.

Next, referring to FIG. 1B, the structure of an exemplary MRI apparatus 4 for carrying out the various embodiments of the invention will be explained in more detail. The MRI apparatus 4 includes a static magnetic field generating system 42, a magnetic field gradient generating system 43, a sequencer 44, a transmitting system 45, a receiving system 46, a signal processing system 47 including an operating section, and a central processing unit (CPU) 48.

The static magnetic field generating system 42 generates a uniform static magnetic field around the subject 2 in a direction of the body axis of the subject 2 or in a direction orthogonal to the body axis of the subject 2. The static magnetic field generating system 42 comprises permanent magnet type, resistive type or superconductive type magnetic field generating means placed in the extended space around the subject 2.

The magnetic field gradient generating system 43 comprises two gradient magnetic field coils 49 which are wound in the three X, Y and Z axis directions, and a gradient magnetic field power source 491 to drive each gradient magnetic field coils 49. When the gradient magnetic field coil power source 491 for each gradient magnetic field coils 49 is driven by a command from the sequencer 44, gradient magnetic fields $G_X$, $G_Y$, and $G_Z$ in the three X, Y and Z axis directions are applied to the subject 2. The way to apply the gradient magnetic fields sets a slice plane relative to the subject 2.

The sequencer 44 repeatedly applies high frequency magnetic field pulses which cause the atomic nucleus of an atom that produces a living tissue of the subject 2 to induce nuclear magnetic resonance, in a predetermined pulse sequence, as described in greater detail below. The sequencer 44 is controlled to operate by the CPU 48, and sends various commands required to collect data of tomogram images of the subject 2 to the transmitting system 45, the magnetic field gradient generating system 43, and a receiving system 46.

The transmitting system 45 irradiates a high frequency magnetic field which causes the atomic nucleus of an atom that produces a living tissue of the subject 2 to induce nuclear magnetic resonance with a high frequency pulses emitted from the sequencer 44. The transmitting system 45 includes a high frequency oscillator 451, a modulator 452, a high frequency amplifier 453, and a high frequency coil 454 for transmitting. The high frequency pulses emitted from the high frequency oscillator 451 are amplitude modulated by the modulator 452 according to the command from the sequencer 44. After the amplitude modulated high frequency pulses are amplified by the high frequency amplifier 453, the pulses are supplied to the high frequency coil 454 positioned close to the subject 2. In this way, an electromagnetic wave is irradiated to the subject 2.

The receiving system 46 detects an echo signal (NMR signal) emitted by the nuclear magnetic resonance in atomic nucleus of the living tissue of the subject 2. The receiving system 46 comprises a high frequency coil 464 for receiving, an amplifier 465, a quadrature phase detector 466, and an A/D converter 467. The electromagnetic wave (NMR signal) from the subject 2 in response to the electromagnetic waves emitted from the high frequency coil 454 for transmitting is detected by the high frequency coil 464 positioned close to the subject 2. The detected NMR signal is input into the A/D converter 467 via the amplifier 465 and the quadrature phase detector 466 to be converted into a digital signal. The quadrature phase detector 466 converts the detected NMR signal into biserial data collected by sampling at timings specified by the command from the sequencer 44. The collected data is transmitted to the signal processing system 47.

The signal processing system 47 includes a CPU 48, a recording device such as a magnetic disc 471 and an optical disc 472, a display 473 such as a CRT, a pointing device and its controller such as a mouse 474, and an input unit such as a key board 475. The CPU 48 performs a Fourier transform operation and an operation of correction coefficient calculation for image reconstruction, and performs appropriate operations based on a signal strength distribution or a plurality of signals of any section to obtain a distribution to create an image, thereby generates a tomogram. The display 473 displays the tomogram.

Such a MRI apparatus 4 with the recent increased performance produces a high magnetic field (e.g. 1.5 T or greater) apparatus, which allows four dimensional image data to be obtained with noise of a practical level and high time resolution.

As noted above, one significant aspect of the various embodiments is reliance on a correlation between water protons and mechanical properties. This correlation is illustrated below with respect to FIGS. 2 and 3.

Figure 2:
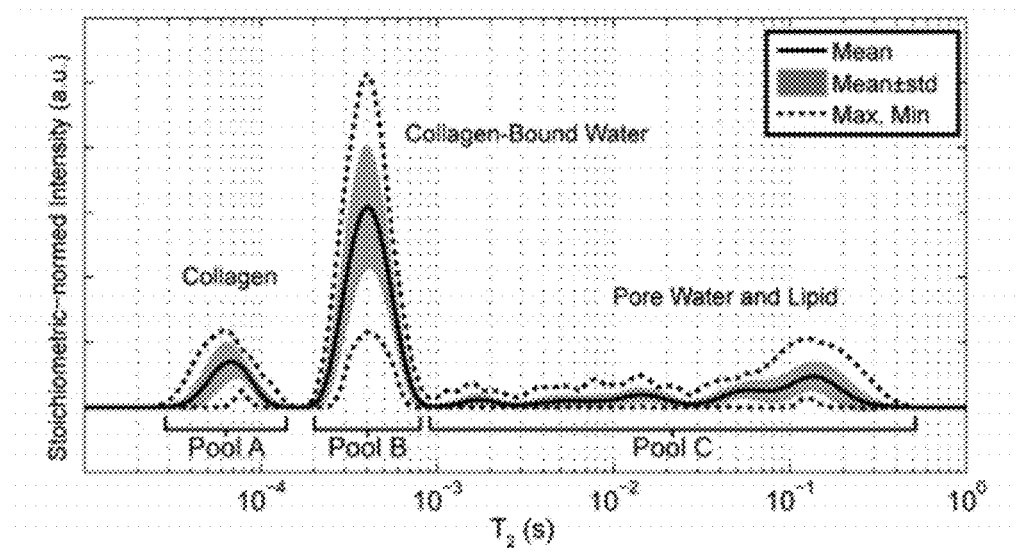
FIG. 2 shows the mean (and standard deviation and range) spectrum of $^1$H NMR transverse relaxation time constants ($T_2$ spectrum) from 40 cadaveric bone samples.

FIG. 2 shows the mean (and standard deviation and range) spectrum of $^1$H NMR transverse relaxation time constants ($T_2$ spectrum) from 40 cadaveric bone samples. In this mean spectrum and in each individual sample spectrum, signals from three distinct domains of $T_2$ are readily identifiable. Signals in the range 50 μs<$T_2$<150 μs, defined herein as pool A, are known to be due primarily to collagen methylene protons. Signals in the range 150 μs<$T_2$<1 ms, defined herein as pool B, are due primarily to collagen-bound water protons. Finally, signals in the range 1 ms<$T_2$<1 s, defined herein as pool C, are known to be due to water protons in pores or lipid protons. From these three signals, six parameters can be extracted: 3 signal amplitudes (SA, SB, SC, expressed as a pool concentration in absolute units of mole $^1$H per liter bone) and 3 corresponding mean relaxation rate constants ($R_{2,A}$, $R_{2,B}$, $R_{2,C}$ in s$^{-1}$).

It is worth noting that while the signal amplitudes are computed as a pool concentration in absolute units of concentration, the correspondence between signal amplitudes, $S_A$, $S_B$, and $S_C$, and actual concentrations of collagen methylene protons, bound water protons, and pore-water or lipid protons, respectively, can be affected by a number of factors. Such factors can include the line shape of the methylene protons, the magnetization exchange rate between bound and methylene protons, and overlap of $T_2$ components from different sources. Accordingly, additional adjustment of the correlation may be necessary. However, for purposes of illustration, it is assumed that the correspondence between the signal amplitudes and the actual concentrations is direct.

Figure 3:
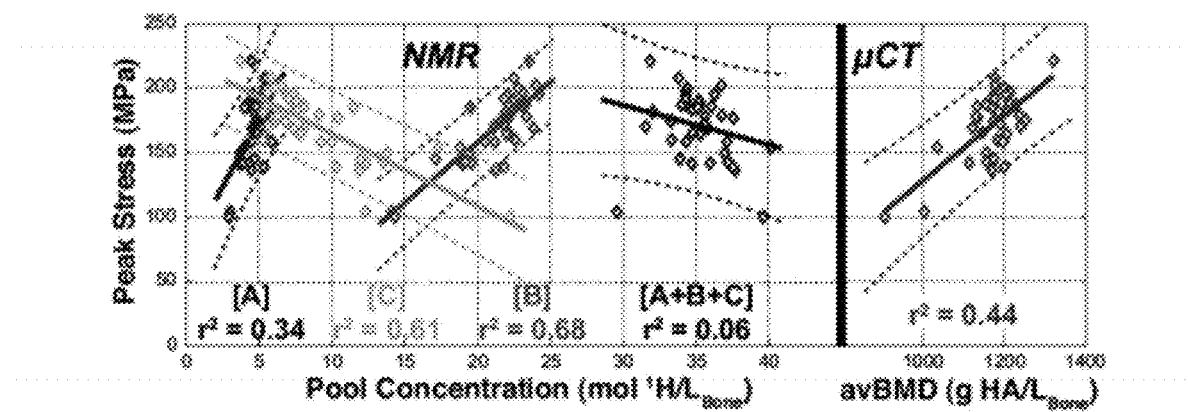
FIG. 3 shows x-y plots of pool concentration for each of pools A-C in FIG. 3 and avBMD for uCT measurements as a function of peak stress of the samples used for FIG. 3.

As shown in FIG. 3, each of the three NMR signal amplitudes ($S_A$, $S_B$, $S_C$) linearly correlates with the mechanical property known as peak stress. FIG. 3 shows x-y plots of pool concentration for each of pools A-C in FIG. 2 as a function of peak stress of the samples used for FIG. 2. Further, FIG. 3 also shows that each of pools A-C correlate linearly with stress of bone ($r^2$=0.34, 0.68, 0.61, p<0.05).

It is worth noting that the sum of all three signals does not provide a correlation ($r^2$=0.06, p>0.05). Similar pair-wise linear correlations (and lack thereof) also existed between NMR signal amplitudes and the other three measured mechanical properties.

In view of the foregoing, FIG. 3 illustrates that peak cortical bone stress, and the other measured mechanical properties, are directly related to the amount of collagen and collagen-bound water in bone, and inversely related to the bone pore volume.

For sake of comparison to conventional techniques, Micro-computed tomography (μCT)-derived measures of bone porosity and the apparent volumetric bone mineral density (avBM D, akin to DXA) of the samples were also obtained. The results of such measurements are shown in a right-hand portion of FIG. 3 for ease of comparison. Although these measurements were found to also linearly correlate with mechanical properties (r2=0.44), it is clear from FIG. 3 that $S_A$ and $S_B$ were better predictors (i.e., higher $r^2$ values) than μCT-porosity for three of four mechanical properties (flexural modulus being the exception), and better predictors than avBMD (i.e., DXA) for all four mechanical properties.

Table 1 summarizes the pairwise linear correlations between imaging measure ($^1$H NMR and X-ray) and the four mechanical properties of principal interest in bone structures.

TABLE 1

A summary of Pearson's $r^2$ for pairwise correlations between imaging measures ($^1$H NMR and X-ray) and mechanical properties.

|  | Yield Stress | Peak Stress | Flexural Modulus | Pre-Yield Toughness |
|---|---|---|---|---|
| $R_{2,A}$ | 0.10 | 0.12 | 0.04* | 0.12 |
| $R_{2,B}$ | 0.19 | 0.22 | 0.12 | 0.19 |

TABLE 1-continued

A summary of Pearson's $r^2$ for pairwise correlations between imaging measures ($^1$H NMR and X-ray) and mechanical properties.

|  | Yield Stress | Peak Stress | Flexural Modulus | Pre-Yield Toughness |
|---|---|---|---|---|
| $R_{2,C}$ | 0.00* | 0.01* | 0.01* | 0.00* |
| $S_A$ | 0.41 | 0.34 | 0.39 | 0.34 |
| $S_B$ | 0.62 | 0.68 | 0.48 | 0.57 |
| $S_C$ | 0.57 | 0.61 | 0.49 | 0.49 |
| $S_A + S_B + S_C$ | 0.05* | 0.06* | 0.06* | 0.03* |
| avBMD | 0.43 | 0.44 | 0.46 | 0.33 |
| Porosity | 0.58 | 0.60 | 0.59 | 0.46 |

It is worth noting that that without the two apparent outlier data (peak stress≈100 MPa), the predictive power of $S_B$ and $S_C$ decreases to $r^2$ values of 0.52 and 0.49. However, without such outliers, the corresponding $r^2$ for avBMD with peak stress decreased to a greater extent. Specifically, the $r^2$ value decreased to 0.16. That is, the relative predictive power of $S_B$ and $S_C$ compared with avBMD increased without these two data points. Multiple linear regression analysis also provides similar results. That is, the combination of NMR signal parameters ($R_B$ and $S_B$) best predicted of three of four mechanical properties (adjusted $r^2$: 0.56-0.70, again, flexural modulus was the exception), and better predicted all four mechanical properties than did avBMD.

Figure 4:
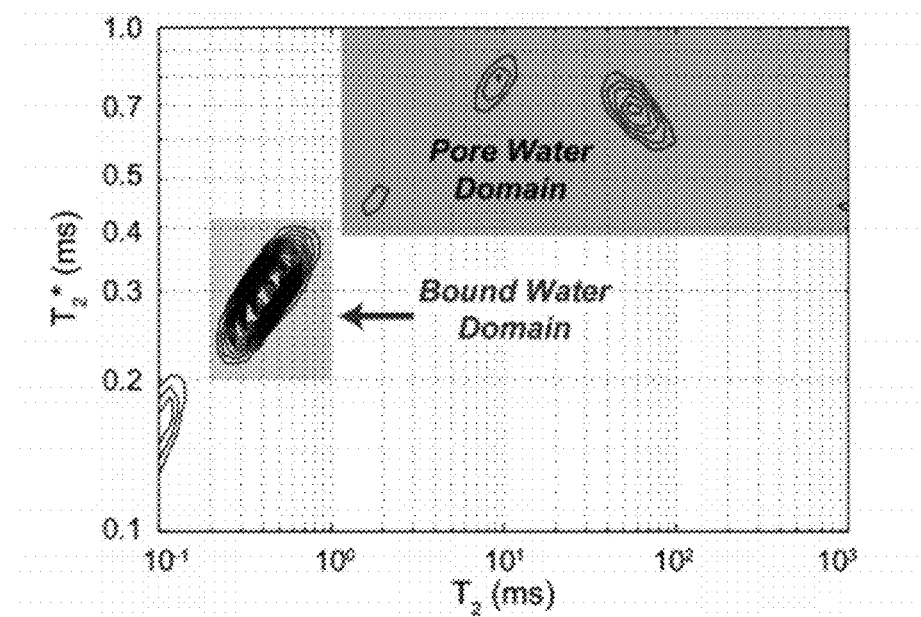
FIG. 4 shows a log-linear plot of $T_2$ versus $T_2^*$ for the samples in FIG. 2.
Figure 5:
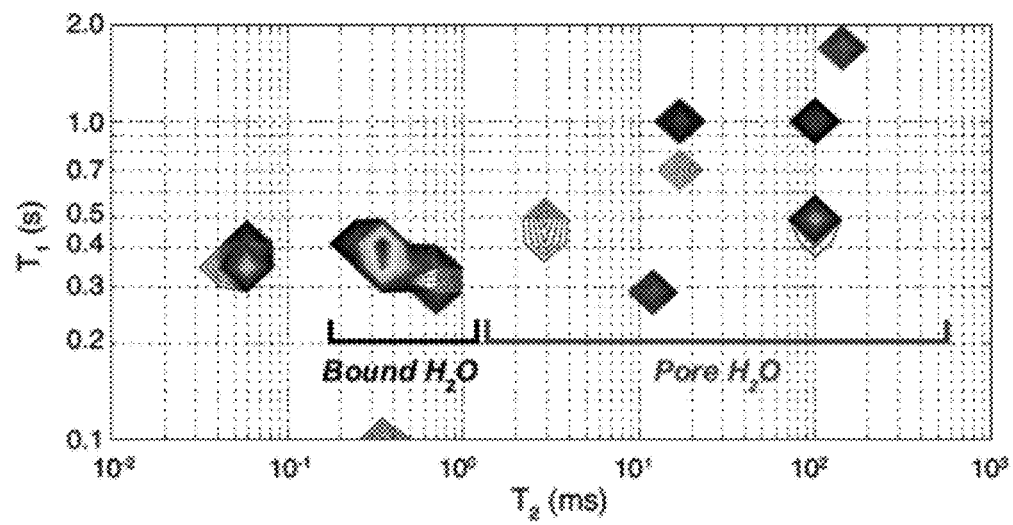
FIG. 5 shows a log-linear plot of $T_2$ versus $T_1$ for the samples in FIG. 2.

In addition to $T_2$ $^1$H NMR signals providing a signal that can be correlated to mechanical properties, the present inventors have found that $T_2$ $^1$H NMR signals also provide superior discriminating characteristics for water protons for different pools. Referring back to FIG. 2, the $T_2$ spectrum shown therein indicates that there is at least a 10× difference between pore water protons and bound water protons in the $T_2$ domain. That is, pore water proton $T_2$ values are at least 10× that of bound water proton $T_2$ values. In contrast, other NMR based relaxation times do not exhibit such discrimination characteristics. For example, FIG. 4 shows a log-linear plot of $T_2$ versus $T_2$* for the samples in FIG. 2. As shown in FIG. 4, the difference in $T_2$* times between pool B (bound water domain) and pool C (pore water domain) is less than 3×. Accordingly, using $T_2$* times for discriminating between different types of water protons would be difficult. FIG. 5 shows a log-linear plot of $T_2$ versus $T_1$ for the samples in FIG. 2. As shown in FIG. 5, the difference in $T_1$ times between pool B (bound water domain) and pool C (pore water domain) is approximately 4×. Accordingly, while using $T_1$ times is possible and superior to using $T_2$* times, for purposes of discriminating between different types of water protons, $T_2$ times would still provide for a greater amount of discrimination and thus would be more useful. Thus, $T_2$ $^1$H NMR signals provide greater discrimination than other relaxation time constants, such as $T_2$* and $T_1$.

In general, current ultrashort echo time (uTE) protocols on human MRI systems use echo times <100 μs, more than short enough to capture the majority of the bound water proton signals and some of the collagen proton signal. Thus, clinical MRI protocols are generally capable of generating $T_2$ signals associated with these features of interest. However, discrimination between bound and pore water protons is typically not achievable using conventional uTE protocols.

Figure 6:
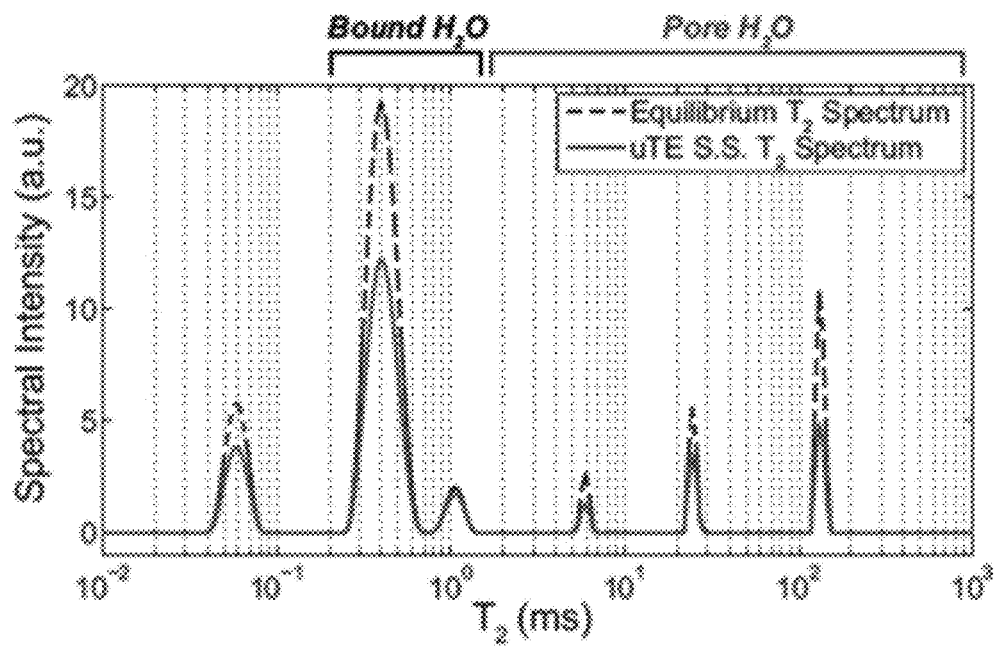
FIG. 6 shows an equilibrium $T_2$ spectrum and a uTE steady state (uTESS) $T_2$ spectrum for a bone specimen.

For example, FIG. 6 shows an equilibrium $T_2$ spectrum and a uTE steady state (uTE SS) $T_2$ spectrum for a bone specimen. The equilibrium $T_2$ spectrum was obtained using a CPMG measurement of the bone specimen, where TE=100 μs, 10000 NE, and TR=15 s. The uTE $T_2$ spectrum was obtained using a 2D uTE pulse sequence with a multiple gradient echo readout configured for cortical bone MRI. That is, soft-tissue suppression was provided with the echo train subtracting from a first echo (associated with bound and pore water proton signals) long $T_2^*$ tissue signals measured from later echoes. In particular, the uTE SS was obtained at 20 C, with TR=35 ms and flip angle=20°. In general, FIG. 6 shows that the uTE SS signal is attenuated with respect to the equilibrium signal. However, the amount of attenuation of pore and bound water proton signals is substantially similar. Accordingly, a $T_2$ signal that discriminates between bound and pore water protons is not generally provided by conventional uTE protocols.

Therefore, it is further necessary to configure uTE protocols to allow the shorter $T_2$ signals from bound water to be discriminated from the longer $T_2$ pore water and lipid signals in vivo. Therefore, strategies for integrating a $T_2$-selective magnetization preparation into a clinically practical uTE-type sequence for in vivo measurements are needed in the various embodiments. One approach in accordance with the various embodiments is to provide a direct measurement of multiple $T_2$ components from bone using multiple spin echoes. Another approach in accordance with the various embodiments is to utilize RF-pulse induced $T_2$ weighting of $^1$H NMR or MRI. An RF pulse that differentially effects the magnetization of $^1$H nuclear spin with different $T_2$ characteristics can be incorporated into almost any MRI method to weight signals from different biophysical origins. Linear combinations of such images/measurements can also be used to further discriminate signals based on $T_2$. In yet another approach in accordance with the various embodiments, $T_1$ weighting of $^1$H NMR or MRI is used. That is, because the multiple $T_2$ components of bone $^1$H NMR exhibit different $T_1$ relaxation time constants, an NMR/MRI method that discriminates signals based on $T_1$ can be used to indirectly discriminate signals based on $T_2$. In still another approach, exchange-discriminated signals can be used. That is, since some $^1$H signal pools (as discriminated by $T_2$) exchange magnetization (on the time-scale of NMR measurements) and others do not, NMR/MRI methods that alter contrast based on this exchange can be used to indirectly discriminate signals based on $T_2$.

Figure 7:
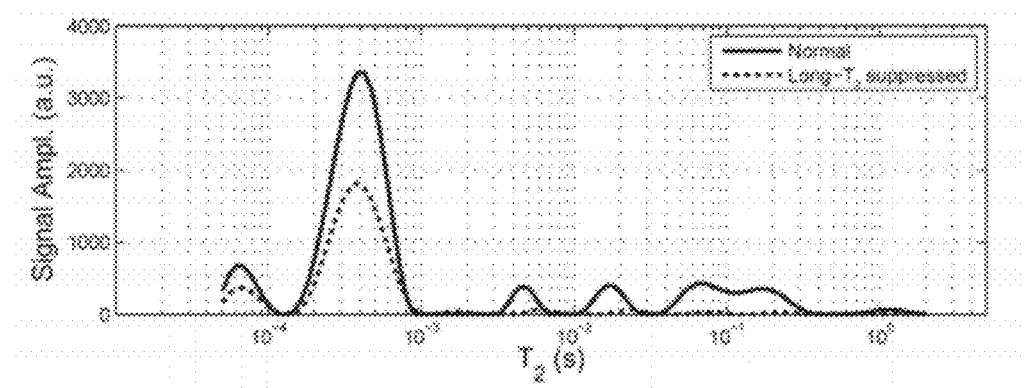
FIG. 7 shows an equilibrium $T_2$ spectrum and a $T_2$ spectrum that results following the complex average of two CPMG signals, with and without a preceding hyperbolic secant radiofrequency (RF) pulse.

As noted above, one strategy is the use of RF pulses to differentially affect the magnetization of protons with different $T_2$ characteristics. The use of such RF pulses is described below. FIG. 7 shows two $T_2$ spectra from one bone specimen. The solid line shows the normal $T_2$ spectrum, while the dotted line shows the spectrum that results following the complex average of two CPMG signals, with and without a preceding hyperbolic secant radiofrequency (RF) pulse. This RF pulse effectively inverts the long $T_2$ signals while largely saturating the collagen proton and bound-water signals, so the complex average cancels only the long $T_2$ signals and results in a net NMR signal that is ≈95% derived from protons with T<1 ms. In other words, the NMR signal from the pore water protons is attenuated to a greater extent than other NMR signals.

Accordingly, in the various embodiments, RF pre-pulses can be provided during MRI imaging, which can be readily integrated into a standard uTE pulse sequence. Thus, the signal intensity obtained from bone structures can be selectively adjusted to rely primarily on bound or pore water protons.

Figure 8:
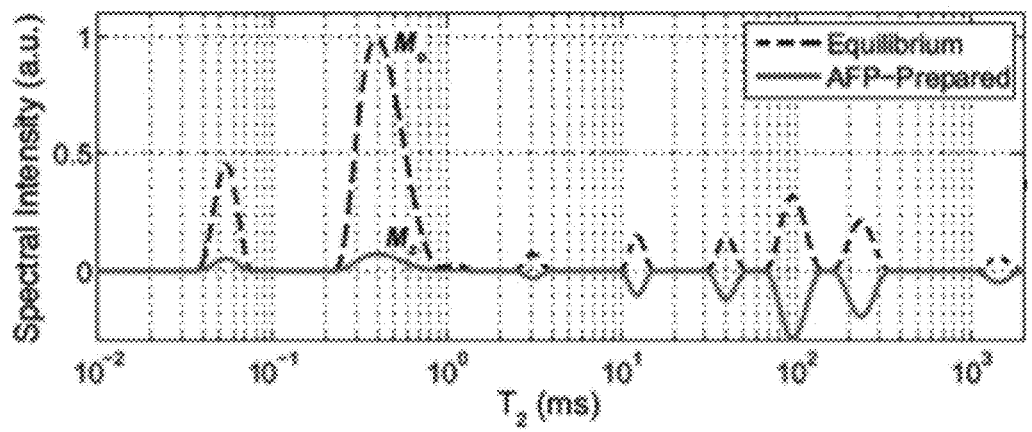
FIG. 8 shows the $T_2$ spectrum for an equilibrium configuration and for an AFP-prepared configuration.
Figure 9:
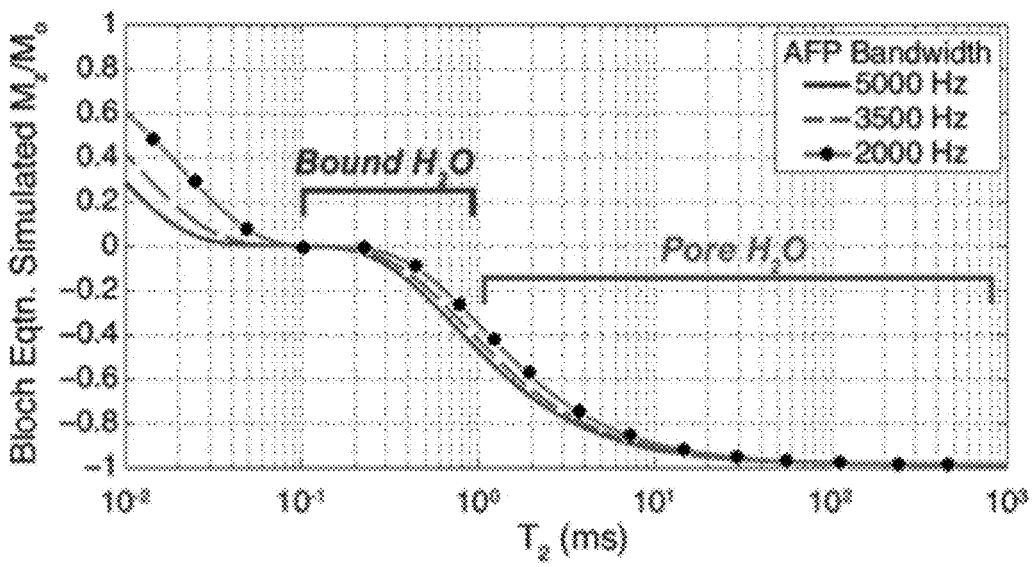
FIG. 9 shows the results of AFP Bloch equation simulations for bandwidths of 2, 3.5 and 5 KHz.

In some embodiments, these RF pulses can be adiabatic pulses, which use both frequency and amplitude modulation of the oscillating magnetic field. An adiabatic pulse that inverts a spin population (with sufficiently long T2) is called an adiabatic full passage (AFP) pulse. For purposes of generating signals for water protons, AFP pulses provide two features of interest, as illustrated in FIGS. 8 and 9. AFP pulses can provide T2 selectivity over a sufficiently large bandwidth (≈2 kHz) to invert cortical bone pore water while saturating cortical bone bound water. FIG. 8 shows the $T_2$ spectrum for an equilibrium configuration and for an AFP-prepared configuration. FIG. 9 shows the results of AFP Bloch equation simulations for bandwidths of 2, 3.5 and 5 KHz. In particular, FIG. 9 is a plot of the ratio of magnetization after AFP ($M_Z$) to the equilibrium magnetization ($M_O$) versus $T_2$. As shown in in FIG. 9, the simulated results first show that the AFP pulse will cause bound water protons to saturate. That is $M_Z/M_O \rightarrow 0$. Second, the AFP pulse will cause long T2 protons, such as pore water protons, to be inverted. That is, $M_Z/M_O \rightarrow -1$. Therefore, AFP pulse can cause the portion of an NMR signal associated with long $T_2$ protons to be significant attenuated and allow bound and pore water protons to be discriminated. Accordingly, by providing AFP pulses with bandwidths greater than or equal to ≈2 kHz and pulse widths greater than or equal to 2 ms, such as 5, 10, or 15 ms, useful manipulation of the NMR signals associated with bound and pore water protons can be achieved.

Figure 10:
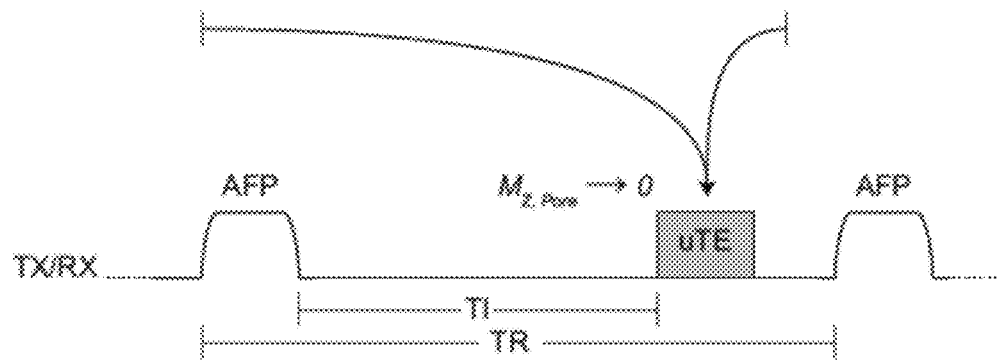
FIG. 10 schematically illustrates a pulse sequence for the AIR SS sequence in accordance with the various embodiments

In these embodiments, the AFP pulses can be provided in several ways. In a first configuration, the AFP pulses can be configured to provide an adiabatic inversion recovery steady state (AIR SS) signal. AIR SS is a uTE imaging strategy in which the uTE SS sequence is modified to include an AFP pulse sequence configured to provide adiabatic inversion and recovery periods. This is schematically illustrated with respect to FIG. 10. As shown in FIG. 10, AFP pulses are provided with a repetition time TR. As noted above, these pulses have a bandwidth ≥2 kHz and a pulse width ≥2 ms in order to saturate the bound water protons and to invert the pore water protons. After an inversion time TI following the AFP pulse, the uTE echo readout is taken. In AIR SS, TI is selected to coincide with the time at which the pore water proton contribution is nulled. This can be a constant value derived from observations of different samples. The result of the AFP SS sequence is illustrated in FIG. 11.

Figure 11:
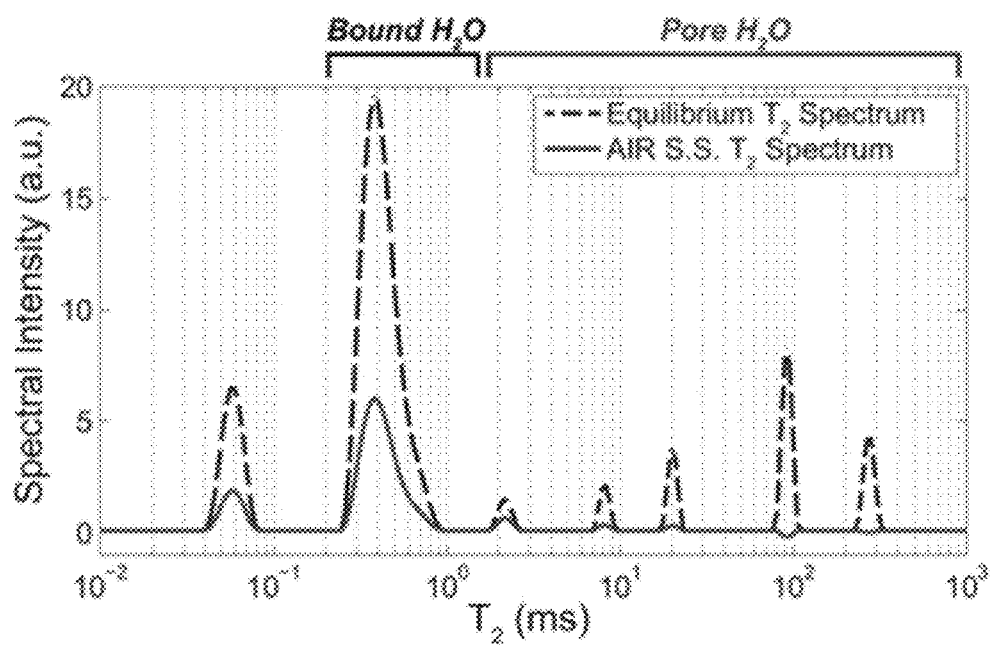
FIG. 11 shows an equilibrium $T_2$ spectrum and an AIR SS $T_2$ spectrum for a bone specimen.

FIG. 11 shows an equilibrium $T_2$ spectrum and an AIR SS $T_2$ spectrum for a bone specimen. The equilibrium spectrum was obtained as previously described. The AIR SS $T_2$ spectrum was obtained at 20 C, using TR=300 ms, TI=90 ms, 20° flip angle, AFP pulse width of 10 ms, and AFP bandwidth of 3.5 kHz. As shown in FIG. 11, the signals associated with pore water protons are significantly attenuated with respect to the signals associated with bound water protons.

Figure 12:
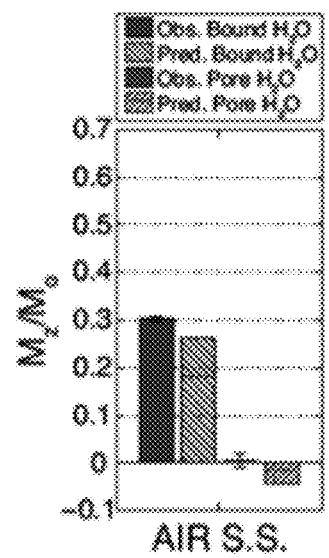
FIG. 12 is a plot of observed and predicted bound and pore water proton concentrations for the AIR SS sequence in accordance with the various embodiments.

Using the spectrum from FIG. 11, the observed $M_Z/M_O$ for bound and pore water can be obtained and compared to predicted $M_Z/M_O$ values obtained using a Bloch model. These results are shown in FIG. 12. As shown in FIG. 12, the observed values appear to the greater than the predicted values. However, this is believed to be due to magnetization transfer with poorly saturated macromolecules ($T_2 <<50$ us) during the inversion period TI. However, in either case the bound water $M_Z/M_O$ is significantly larger than the pore water $M_Z/M_O$. Accordingly, the assumption can be made that the net NMR signal from the AIR SS sequence is due to bound water.

Further, a Bland-Altman analysis of the AIR SS derived bound water concentration versus equilibrium CPMG derived bound water concentration also shows a net positive bias, as shown in FIG. 13. FIG. 13 is an x-y plot of CPMG-derived bound water proton concentration versus AIR SS derived bound water proton concentration. The net positive bias is believed to be due to the bias shown in FIG. 12. However, as shown in FIG. 13, a correlation with $r^2=0.93$ is shown. Therefore, this confirms that the AIR SS derived bound water proton concentration is proportional to the equilibrium CPMG derived bound water proton concentration.

Further, the correlation also confirms that a universal TI can be used. That is, an average TI of existing samples can be used for new samples.

However, the various embodiments are not limited to solely the sequence illustrated in FIG. 10. In other configurations, a double-AFP steady-state (DAFP SS) sequence can be used. In such a configuration, at the beginning of the repetition period, two AFIP pulses are provided in immediate succession, followed by an immediate uTE readout. At the end of the repetition period, the process can be repeated. This is schematically illustrated with respect to FIG. 14. In the DAFP SS sequence, the result of the two pulses is to cause bound water protons to be strongly saturated, similar to the AIR SS sequence. However, the additional pulse causes the pore water protons to be inverted twice, effectively providing a zero degree flip. The result of this sequence is illustrated in FIG. 15.

Figure 14:
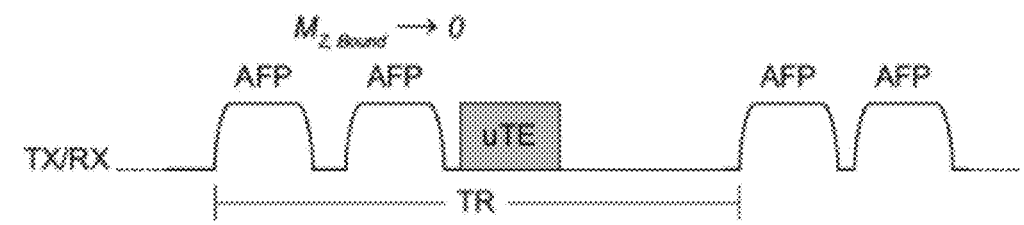
FIG. 14 schematically illustrates a pulse sequence for the AIR SS sequence in accordance with the various embodiments
Figure 15:
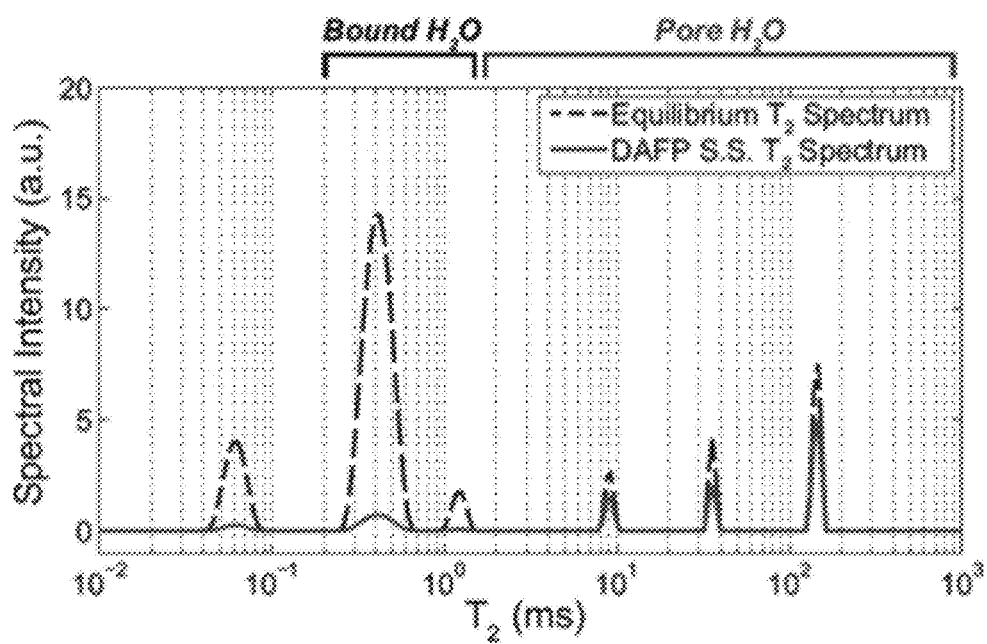
FIG. 15 shows an equilibrium $T_2$ spectrum and a DAFP SS T2 spectrum for a bone specimen.

FIG. 15 shows an equilibrium $T_2$ spectrum and a DAFP SS T2 spectrum for a bone specimen. The equilibrium spectrum was obtained as previously described. The DAFP SS $T_2$ spectrum was obtained at 20 C, using TR=300 ms, TI=0 ms, DAFP pulse width of 20 ms, and DAFP bandwidth of 3.5 kHz. The DAFP pulse in this example is comprised of two 10 ms AFP pulses with no separation in between. As shown in FIG. 14, the signals associated with bound water protons are significantly attenuated with respect to the signals associated with pore water protons. That is, while the bound water protons are nearly saturated, the pore water signal is only slightly attenuated by the DAFP, due to relaxation during the pulse.

In the various embodiments, the time between pulses and the time between the second pulse and acquisition can vary. Typically, such times are dictated, in part, by the equipment being used. That is, no minimum separation necessary, as the minimum amount of time between pulses or between the second pulse and acquisition is limited only by the capabilities of the imaging system. With respect to a maximrrurm time, these times can be more sensitive to the T1 values for the pore water protons and the bound water protons. For example, the delay between pulses is preferably less than the T1 time for pore water protons. In one embodiment, this delay between pulses can be less than ⅒ of T1 for pore water protons. For the delay between the second pulse and acquisition, the delay is preferably less than the T1 of bound water protons. In one embodiment, this delay between pulses can be less than ⅒ of T1 for pore water protons. However, the various embodiments are not limited solely to the pulse sequences using these values. Rather any pulse sequence thats provide sufficient discrimination between T2 values can be used in the various embodiments.

Figure 16:
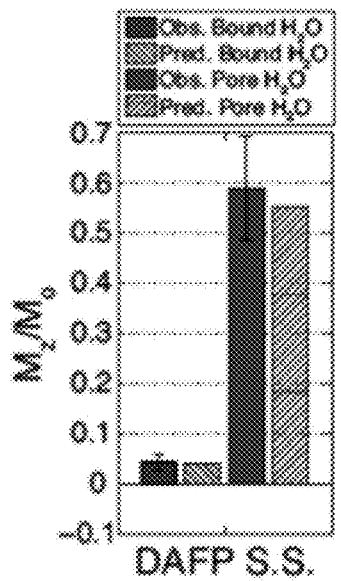
FIG. 16 is a plot of observed and predicted bound and pore water proton concentrations for the DAFP SS sequence in accordance with the various embodiments.

Using the spectrum from FIG. 15, the observed $M_z/M_O$ for bound and pore water protons can also be obtained and compared to predicted $M_z/M_O$ values obtained using a Bloch model. These results are shown in FIG. 16. As shown in FIG. 16, the observed values appear to the close to the predicted values. However, the pore water $M_z/M_O$ is significantly larger than the bound water $M_z/M_O$. Accordingly, the assumption can be made that the net NMR signal from the DA FP SS is due to pore water protons.

Figure 17:
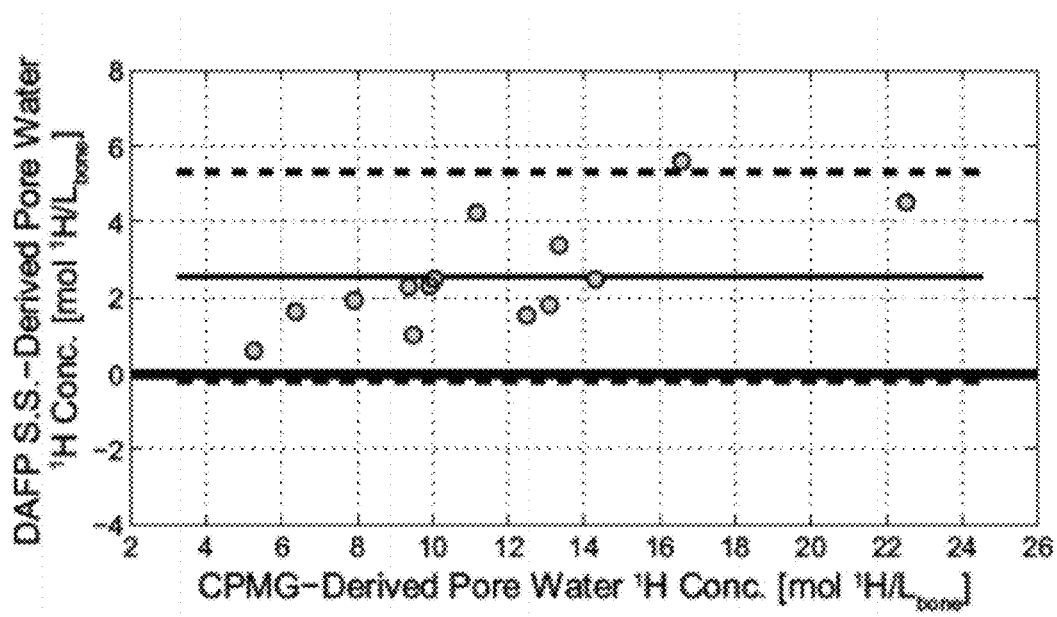
FIG. 17 is an x-y plot of CPMG-derived pore water proton concentration versus DAFP SS derived pore water proton concentration.

Further, a Bland-Altman analysis of the DAFP SS derived pore water concentration versus equilibrium CPMG bound water concentration shows a net positive bias, as shown in FIG. 17. FIG. 17 is an x-y plot of CPMG-derived pore water proton concentration versus DAFP SS derived pore water proton concentration. The net position bias is believed to be due to incomplete bound water saturation and possible pore water T variations. However, as shown in FIG. 17, a correlation with $r^2=0.97$ is shown. Therefore, this confirms that the DAFP SS derived pore water proton concentration is proportional to the equilibrium CPMG derived pore water proton concentration.

Although the discussion above shows that $T_2$ $^1H$ NMR signals associated with bound or pore water protons can be correlated to mechanical properties of bone structures and that AIR SS and DAFP SS sequences can be used to generated $T_2$ $^1H$ NMR signals that discriminate between bound and pore water protons, in the clinical setting there is needed a methodology for obtaining the water proton concentrations without having to obtain an equilibrium sample. In the some embodiments, this can be obtained by using the AIR SS or DAFP SS techniques during MRI imaging of a region of interest and a reference sample. This is described below with respect to FIG. 18.

Figure 18:
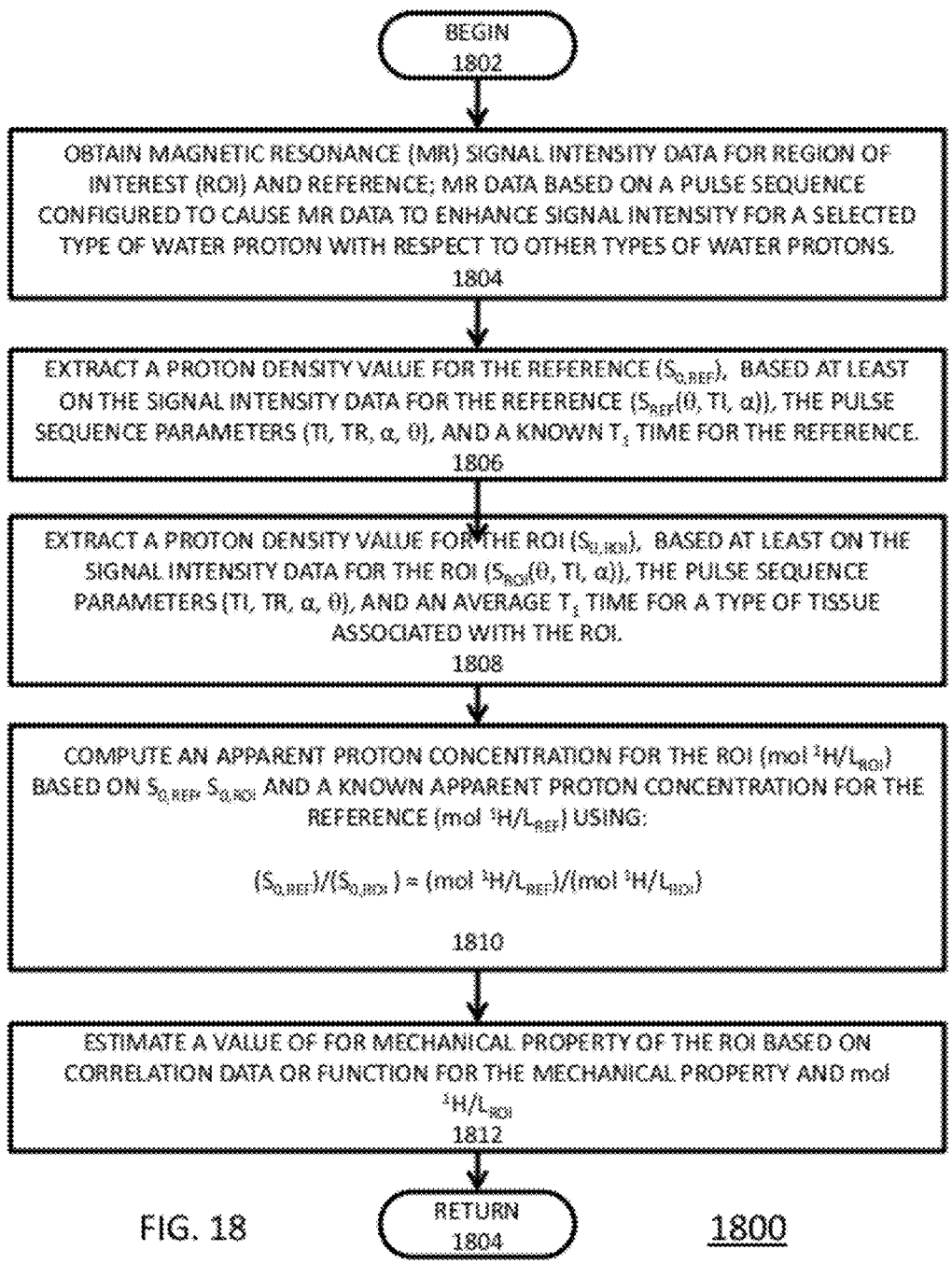
FIG. 18 is a flowchart of steps in an exemplary method 1800 for estimating the mechanical properties of a bone structure.

FIG. 18 is a flowchart of steps in an exemplary method 1800 for estimating the mechanical properties of a bone structure. The method 1800 begins at step 1802 and continues on to step 1804. At step 1804, NMR signal intensity data is obtained for a region of interest (ROI) and a reference sample. In the various embodiments, the reference sample can be any type of sample that has been previously characterized. For example, a reference sample can be a water phantom or marker. However, the various embodiments are not limited in this regard and any other type of reference sample can be used. The NMR signal intensity data obtained at step 1804 can generated by using an MRI pulse sequence configured to provide a signal intensity primarily due to bound water protons or pore water protons. For example, a uTE MRI pulse sequence modified to include an AIR SS or DAFP SS sequence, as previously described. However, the various embodiments are not limited in this regard and any other type of MRI pulse sequences that results in NMR signal intensity data that is primarily due to a type of water proton correlating to a mechanical property can be used in the various embodiments.

Once the NMR data is obtained at step 1804, the method 1800 can proceed to steps 1806 and 1808. In steps 1806 and 1808, unweighted signal amplitude values [[IS THIS THE CORRECT TERM?]], proportional to proton density, are obtained for the reference and the ROI. In particular, the unweighted signal amplitude values are obtained based on the $T_1$-weighting corrected signal equation:

$$S(\theta, TI, TR) = S_0 \frac{1-(1-\alpha)e^{-TI/T1} - \alpha e^{-TR/T1}}{1-\alpha e^{-TR/T1}\cos\theta} \quad (1)$$

where $S_0$ the unweighted signal amplitude value, $S(\theta,TI,TR)$ is the signal intensity value from the NMR data, $\theta$ is the excitation flip angle, TR is the repetition time for the pulse sequence, TI is the inversion time, $\alpha$ is a parameter describing the AFP pulse effects on longitudinal magnitude ($-1 \le \alpha \le 1$). In the various embodiments, the values for TI, $T_1$ and $\alpha$ need not be obtained from the ROI. Rather, average values for TI, $T_1$ and $\alpha$ derived from research studies on similar samples for bound or pore water can be used.

Referring back to FIG. 18, at step 1806 the unweighted signal intensity value for the reference ($S_{0,REF}$) is obtained using the NMR data associated with the reference ($S_{REF}(\theta, TI,TR)$), the pulse sequence parameters ($\theta,TI,TR$), and the known $T_1$ time and a for the type of water proton in the reference to solve equation 1 for $S_{0,REF}$. Similarly, at step 1808, the unweighted signal intensity value for the ROI ($S_{0, ROI}$) is obtained using the NMR data associated with the reference ($S_{ROI}(\theta,TI,TR)$), the pulse sequence parameters (θ,TI,TR), and the known Ti time and a for the type of water proton in the ROI to solve equation 1 for $S_{0,ROI}$.

After $S_{0,REF}$ and $S_{0,ROI}$ are obtained at steps 1806 and 1808, respectively, an apparent proton concentration for the ROI can be computed at step 1810. In particular, since the unweighted signal intensity values for the reference and ROI will be proportional to their corresponding proton densities, the ratio of the unweighted signal intensity values for the reference and the ROI will be proportional to the ratio of the proton density or concentration in the reference (mol $^1H/L_{REF}$) and the ROI (mol $^1H/L_{ROI}$). Accordingly, using the relationship:

$$(S_{0,REF})/(S_{0,ROI}) \approx (\text{mol } ^1H/L_{REF})/(\text{mol } ^1H/L_{ROI}), \quad (2)$$

the unweighted signal intensity values from steps 1806 and 1808, and the known proton density for the reference, the proton density for the ROI can be estimated.

Once the proton density for the ROI is obtained at step 1810 using equation 2, the proton density for the ROI can be used with correlation data, such as that in FIG. 2 or Table 1, to determine the mechanical properties of the bone structures at step 1812. Thereafter, the method 1800 can end at step 1814.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method, comprising:
   obtaining $^1H$ signals-associated with a bone structure for a range of $T_2$ values by applying a pulse sequence configured to cause bone tissue to generate the $^1H$ signals corresponding to the range of $T_2$ values, the $^1H$ signals comprising nuclear magnetic resonance (NMR) signals or magnetic resonance imaging (MRI) signals;
   computing one or more signal parameters from the $^1H$ signals, each of the signal parameters comprising a signal amplitude for a pre-defined sub-range of $T_2$ values corresponding to a proton type within the range of $T_2$ values; and
   determining at least one of mechanical properties or fracture risk for the bone structure based on the signal parameters and stored correlation data that correlates the at least one of the mechanical properties or the fracture risk to values to each of the signal parameters.

2. The method of claim 1, wherein the bone structure comprises a first of a plurality of bones structures in a patient, wherein the method further comprises:
   estimating mechanical properties or fracture risk for a second of the plurality of bone structures in the patient based on the mechanical properties or fracture risk for the first of the plurality of bones structures.

3. The method of claim 1, wherein the step of obtaining further comprises:
   obtaining the $^1H$ signals using a multiple spin echo pulse sequence.

4. The method of claim 1, wherein the step of obtaining further comprises:
   obtaining the $^1H$ signals using an RF-pulse induced $T_2$ weighting as preparation for another pulse sequence.

5. The method of claim 1, wherein the step of obtaining further comprises:
   obtaining the $^1H$ signals using $T_1$ weighting as preparation for another pulse sequence.

6. The method of claim 1, wherein the step of obtaining further comprises:
   obtaining the $^1H$ using magnetization exchange as preparation for another pulse sequence.

7. The method of claim 1, wherein the computing of the one or more signal parameters comprises calculating the signal amplitude as a concentration of the proton type associated with the pre-defined sub-range of $T_2$ values corresponding to the proton type based on the $T_2$ values in the pre-defined sub-range of $T_2$ values.

8. The method of claim 1, wherein the proton type for at least one of the signal parameters comprises collagen-bound water protons, water protons in pores, or lipid protons.

9. A system, comprising:
   an imaging device for generating $^1H$ signals associated with a bone structure for a range of $T_2$ values by applying a pulse sequence configured to cause bone tissue to generate the $^1H$ signals corresponding to the range of $T_2$ values, the $^1H$ signals comprising nuclear magnetic resonance (NMR) signals or magnetic resonance imaging (MRI) signals;
   a processing element communicatively coupled to the imaging device, wherein the processing element is configured for computing one or more signal parameters from the $^1H$ signals, each of the signal parameters comprising a signal amplitude for a pre-defined sub-range of $T_2$ values corresponding to a proton type within the range of $T_2$ values, and determining at least one of mechanical properties or fracture risk for the bone structure based on the signal parameters and stored correlation data that correlates the at least one of the mechanical properties or the fracture risk to each of the signal parameters.

10. The system of claim 9, wherein the bone structure comprises a first of a plurality of bones structures in a patient, wherein the processing element is further configured for estimating mechanical properties or fracture risk for a second of the plurality of bone structures in the patient based on the mechanical properties or fracture risk for the first of the plurality of bones structures.

11. The system of claim 9, wherein the imaging device is configured for obtaining the $^1$H signals using a multiple spin echo pulse sequence.

12. The system of claim 9, wherein the imaging device is configured for obtaining the $^1$H signals using an RF-pulse induced $T_2$ weighting as preparation for another pulse sequence.

13. The system of claim 9, wherein the imaging device is configured for obtaining the $^1$H signals using $T_1$ weighting as preparation for another pulse sequence.

14. The system of claim 9, wherein the imaging device is configured for obtaining the $^1$H signals using magnetization exchange as preparation for another pulse sequence.

15. The system of claim 9, wherein the processing element is configured for computing the one or more signal parameters by calculating the signal amplitude as a concentration of the proton type associated with the pre-defined sub-range of $T_2$ values corresponding to the proton type based on the $T_2$ values in the pre-defined sub-range of $T_2$ values.

16. The system of claim 9, wherein the proton type for at least one of the signal parameters comprises collagen-bound water protons or water protons in pores, or lipid protons.

\* \* \* \* \*